United States Patent [19]

Hernandez

[11] Patent Number: 4,812,127
[45] Date of Patent: Mar. 14, 1989

[54] DENTAL HYGIENE TEACHING TOOL AND STORAGE DEVICE

[76] Inventor: Samson V. Hernandez, 44 W. 10th Dr., Mesa, Ariz. 85202

[21] Appl. No.: 129,597

[22] Filed: Dec. 7, 1987

[51] Int. Cl.⁴ .............................................. G09B 23/28
[52] U.S. Cl. ..................................... 434/264; 132/309; 132/310
[58] Field of Search .................. 434/238, 264; 132/91, 132/92 R, 92 A, 93; 433/54, 64

[56] References Cited

U.S. PATENT DOCUMENTS

| | | | |
|---|---|---|---|
| 1,598,052 | 8/1926 | Chayes | 434/264 |
| 1,916,376 | 7/1933 | Kohler | 434/264 |
| 2,730,805 | 1/1956 | Smolka | 434/264 |
| 2,926,487 | 3/1960 | Stone | 434/238 X |
| 4,073,071 | 2/1978 | Angelotti | 434/267 X |
| 4,221,060 | 9/1980 | Moskowitz et al. | 434/264 |
| 4,231,181 | 11/1980 | Fabricant | 434/264 X |
| 4,635,660 | 1/1987 | Graves | 132/92 A |
| 4,734,033 | 3/1988 | Huffman | 433/64 X |

Primary Examiner—Ira S. Lazarus
Assistant Examiner—Peggy Neils
Attorney, Agent, or Firm—Louise S. Heim

[57] ABSTRACT

A dental hygiene teaching tool and storage device is configured as a caricatured head including a lower jaw member and an upper jaw member which is movably positioned on top of the lower jaw member. The forward portions of both the lower and upper jaw members are molded to simulate realistic human teeth. The lower jaw member includes a well for receiving a container of dental floss which is normally covered and concealed by the upper jaw member. The upper jaw member includes a plurality of bores for holding elongated dental hygiene implements such as toothbrushes, mouth mirrors and the like in vertically upright positions.

6 Claims, 2 Drawing Sheets

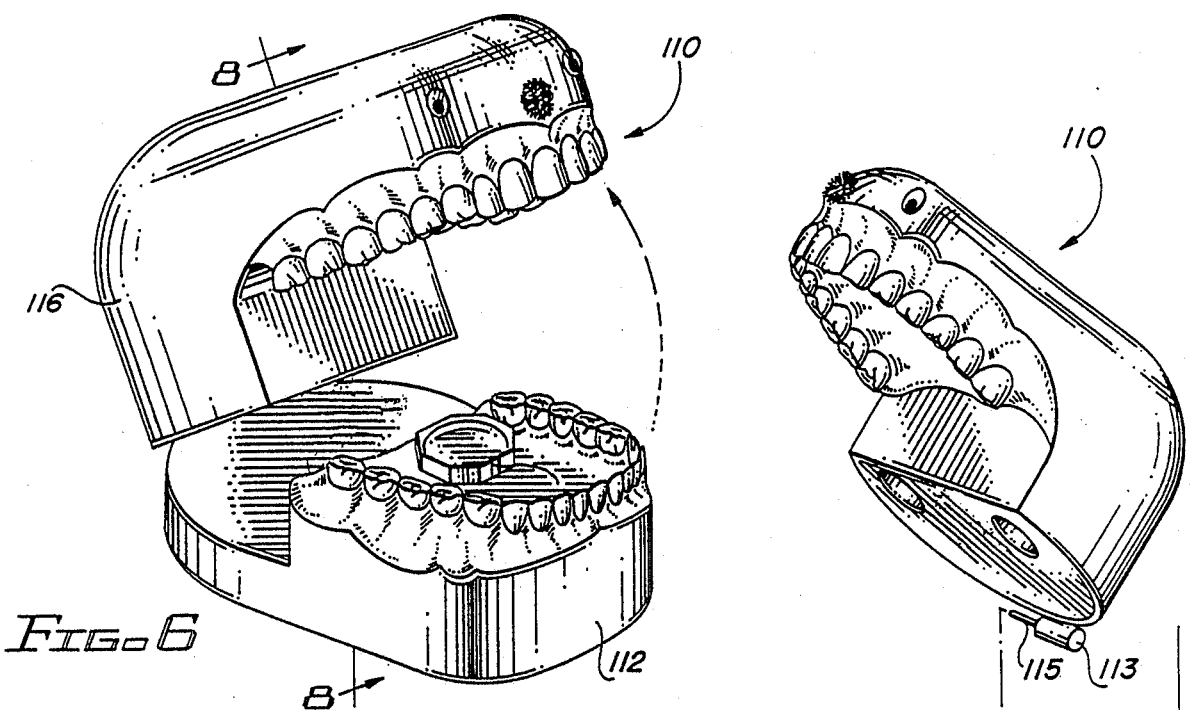
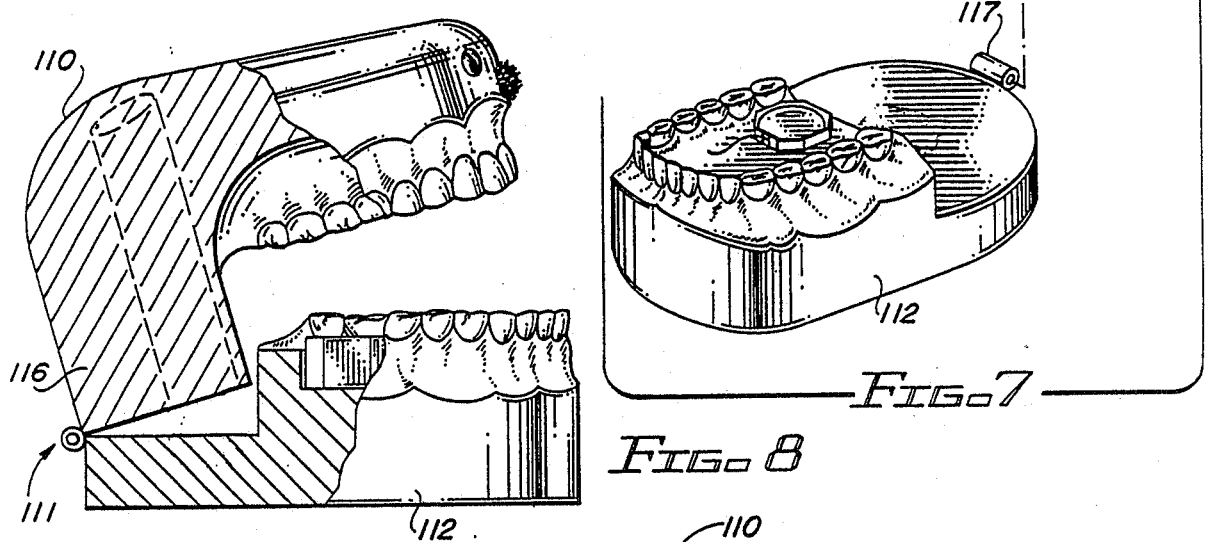
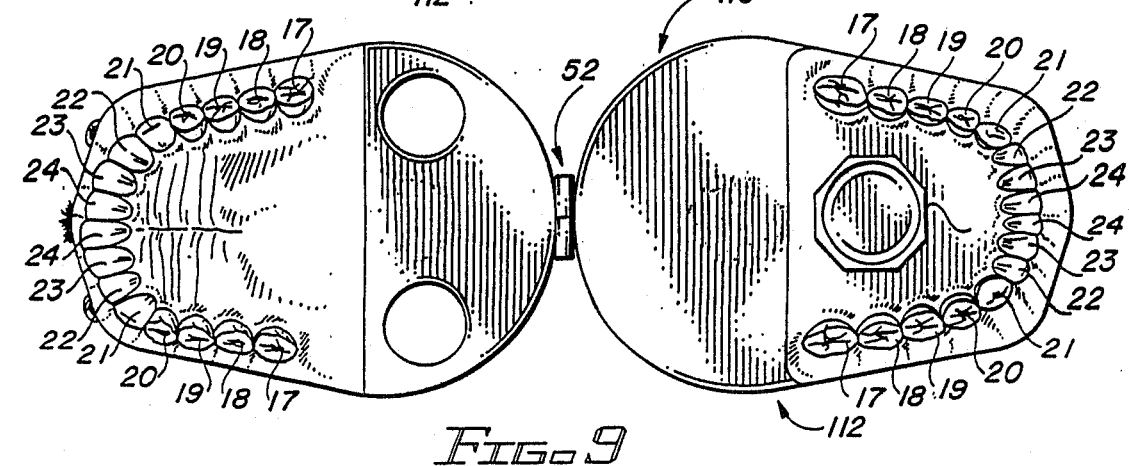

DENTAL HYGIENE TEACHING TOOL AND STORAGE DEVICE

CROSS-REFERENCE TO RELATED APPLICATION

This application is related to my co-pending design patent application filed Aug. 12, 1987 and assigned Ser. No. 085,331.

BACKGROUND OF THE INVENTION

1. Field of the Invention

This invention relates in general to dental hygiene educational tools and, more particularly, to a device for stimulating a child's interest in dental hygiene while at the same time serving as a holder for storing dental hygiene equipment such as toothbrushes, mouth mirrors and dental floss.

2. Description of the Prior Art

Dental hygiene educational tools can be grouped into two major categories. The first category includes professional teaching tools such as demonstrator models which are used for teaching dental students and technicians how to make dentures, or to demonstrate proposed tooth repairs to adult patients. Representative samples of this first category of dental hygiene educational tools can be found in U.S. Pat. No. 1,711,947 to Ingwersen, U.S. Pat. No. 1,916,376 to Kohler, U.S. Pat. No. 2,333,795 to Kellerman et al, and U.S. Pat. No. 2,730,805 to Smolka. The demonstration kit of Kellerman et al also provides a secondary function as a storage device since a number of pockets and a receptacle are provided for receiving articles such as inlays and amalgams. However, the structural complexity of the device of Kellerman et al, as well as of the other demonstrator models in the patent referred to above, makes them unsuitable for use by children or for other domestic applications.

The second category of dental hygiene educational tools includes toys and the like which are specifically directed at children. Representative devices from this second category are disclosed in U.S. Pat. No. 2,926,487 to Stone, and U.S. Pat. No. 4,231,181 to Fabricant. The patent to Stone is directed to a toothbrush holder provided with a caricatured representation of the face of an animal or other figure and including a representation of the teeth of the figure. The figure is also provided with a movable hand holding a simulated toothbrush. A mechanical mechanism is included within the device for reciprocating the movable hand and simulated toothbrush, causing the figure to "brush" its teeth for a predetermined length of time. The object of the device is to encourage a child to brush his or her teeth by mimicking the movements of the caricatured figure, and also to serve as a timer for indicating how long the child should continue to brush. One drawback of the device is that the mechanical mechanism for reciprocating the simulated toothbrush is somewhat complex, making the device costly and subject to breakdown. Another drawback is that because the figure is intended to be a caricature, the device has no instructional value as far as teaching children about the real structure or anatomy of their teeth and mouth. Still another drawback is that the device includes only a single hook for supporting a toothbrush. No means are provided holding additional toothbrushes or other dental hygiene equipment such as a mouth mirror or dental floss.

The patent to Fabricant discloses a dental toy including two simulated jaws hinged to each other for movement between open and closed positions. Each jaw carries a plurality of pockets for accommodating the roots of simulated teeth, which a child can make from a soft moldable material such as clay. Simulated dental tools such as a drill, a dental mirror and tooth-holding tongs can also be included with the top to allow the child to play dentist by pretending to drill, fill cavities, pull teeth and perform other such dental activities. This toy is relatively complex and expensive to manufacture and includes a large number of loose parts which can easily get lost. In addition, it does not include means for storing dental hygiene equipment such as toothbrushes and dental floss.

Accordingly, a demand exists for a new and useful dental hygiene teaching tool and storage device which overcomes some of the shortcomings of the prior art.

SUMMARY OF THE INVENTION

In accordance with the present invention, a new and useful dental hygiene teaching tool is provided in the form of a storage device for holding dental hygiene equipment such as toothbrushes, mouth mirrors and dental floss.

The device comprises a caricatured head including lower jaw member having a flat bottom surface for supporting the device on a level area such as a table or sink top, and an upper jaw member movably positioned on top of the lower jaw member. The forward portions of both the lower and upper jaw members are modeled to simulate human teeth and gums in a realistic and orthodontically correct fashion. In addition, a pair of eyes and a nose are provided on the front portion of the upper jaw member just above the gums to provide the device with a whimsical, cartoon-like appearance which appeals to children.

The top rear portion of the upper jaw member is provided with a plurality of bores or through-holes for holding elongated dental hygiene implements such as a toothbrush, a mirror or the like in a vertically upright position. Similarly, the floor area of the lower jaw includes a well for receiving a container of dental floss.

In a first embodiment of the invention, the upper jaw member is normally supported in a stable position on the lower jaw member by means of a tapering peg which depends from the lower rear surface of the upper jaw member and is received in a mating socket in the top rear surface of the lower jaw. The upper jaw may be removed from the lower jaw simply by lifting on the upper jaw until the peg is withdrawn from the source.

In a second embodiment of the invention, the upper jaw is hingedly connected to the lower jaw to enable a user to simulate the actual biting or talking movements performed by human jaws. A demountable hinge arrangement may be used to enable the upper jaw to be lifted completely off the lower jaw or a nondemountable arrangement may be used if complete removal of the upper jaw is not desired.

The device may be provided as part of a kit along with an educational booklet including diagrams of the teeth and gums, and illustrating proper brushing and flossing techniques. Dental patients will thus be able to directly relate the diagrams in the book to the actual models of the teeth on the lower and upper jaw members, which will in turn increase their awareness and knowledge of their own teeth and gums, and encourage them to develop good dental habits.

Accordingly, it is an object of the present invention to provide a dental hygiene teaching tool in the form of a storage device for holding toothbrushes, mouth mirrors, dental floss and the like.

Another object of the invention is to provide a dental hygiene storage device configured as a caricatured head including movable jaw members having realistic, orthodontically correct teeth and gums.

Yet another object of the device is to provide an appealing, educational dental hygiene equipment storage device which is durable, yet inexpensive and simple to manufacture and suitable for use by children.

The foregoing and other objects of the present invention, as well as the invention itself, may be more fully understood from the following description when read in conjunction with the accompanying drawings.

BRIEF DESCRIPTION OF THE DRAWINGS

FIG. 6 is a perspective view showing an alternative embodiment of the invention.

FIG. 7 is a perspective view showing the jaw members of the device of FIG. 6 in exploded relation to one another.

FIG. 8 is a sectional view taken through line 8—8 of FIG. 6.

FIG. 9 is a plan view of the device showing the jaw members in a fully open position.

DESCRIPTION OF THE PREFERRED EMBODIMENTS

Figure 1:
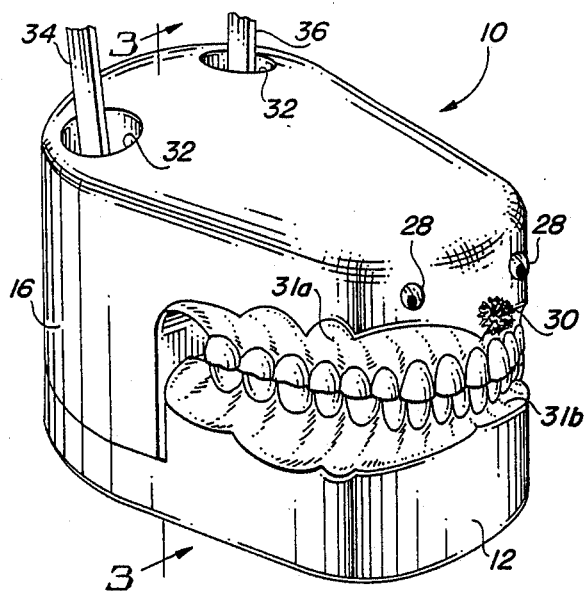
FIG. 1 is a perspective view showing the teaching tool and storage device of the present invention.

Referring more particularly to the drawings, the teaching tool and storage device of the present invention, indicated in its entirety by the numeral 10, comprises a caricatured head including a lower jaw member 12 having a flat bottom surface 14 for supporting the device on a level area such as a table or sink top (not shown) and an upper jaw member 16 movably positioned on top of the lower jaw member 12. Each of the jaw members 12, 16 is preferably molded from a lightweight, inexpensive yet durable synthetic material such as plastic, which is suitable for mass-production. The forward portions of both the lower and upper jaw members 12, 16 are molded to simulate human teeth and gums in a realistic and orthodontically correct fashion. For instance, each jaw is preferably symmetrical about a central axis (not shown) which divides the jaw into a left side and a right side. Each side of each jaw includes three molars 17, 18, 19, two bicuspids, 20, 21, a cuspid 22, a lateral tooth 23 and a central tooth 24 all of which are preferably permanently anchored in said gums. The palate portion of the upper jaw 16 is preferably also realistically formed, and includes such details as the ridges or rugae 26 on the roof of the mouth. In addition, a pair of eyes 28 and a nose 30 are provided on the front portion of the upper jaw member just above the upper gums 31a to provide the device with a whimsical, cartoon-like appearance which appeals to children. Furthermore, the figure is preferably portrayed without lips. The omission of lips from the face serves not only to heighten the whimsicality of the figure, but also allows a clear, unobstructed view of the realistic detail of the figure's upper and lower gums 31a and 31b which form an important part of this invention.

The top rear portion of the upper jaw member 16 is provided with a plurality of bores or through-holes 32 for supporting the stems of elongated dental hygiene implements 34, 36 such as toothbrushes, mouth mirrors and the like. Similarly, the floor area 38 of the lower jaw 12 includes a well 40 for receiving a container of dental floss 42. The well 40 is shown here as being octagonal in shape in order to conform to the shape of one commercially available floss container 42 which is in widespread use. However, the geometrical configuration of the well 40 is not a critical feature of the present invention, since wells of other shapes and dimensions could also be provided to correspond to the shapes of other commercially available floss containers.

Figure 2:
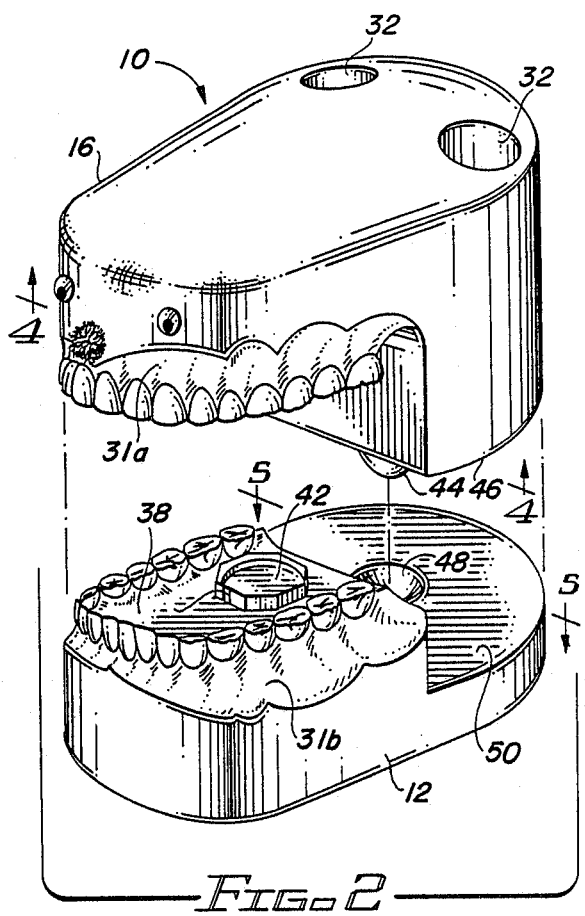
FIG. 2 is a perspective view showing the jaw members of the device in exploded relation to one another.
Figure 3:
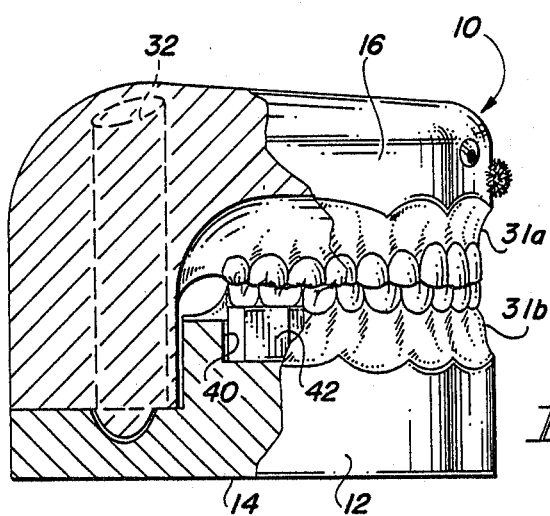
FIG. 3 is a sectional view taken through line 3—3 of FIG. 1.
Figure 4:
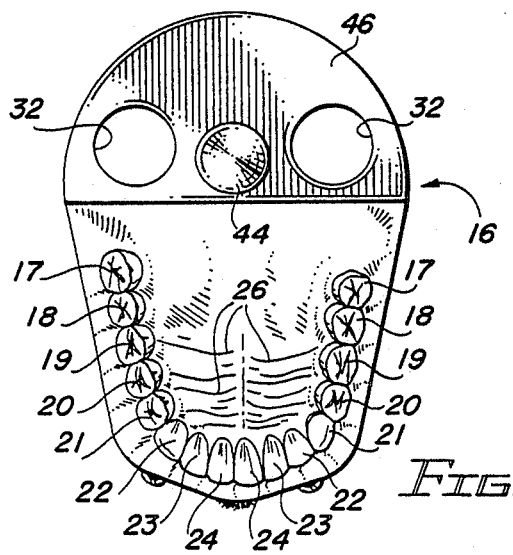
FIG. 4 is a view through line 4—4 of FIG. 2.
Figure 5:
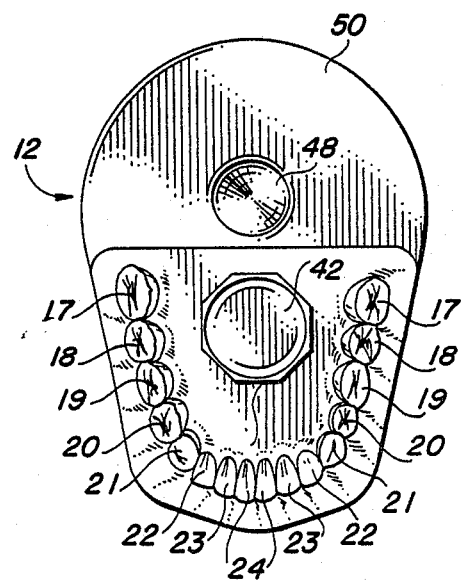
FIG. 5 is a top view taken through line 5—5 of FIG. 2.

In a first embodiment of the invention shown in FIGS. 1-5, the upper jaw member 16 is normally supported in a stable position on the lower jaw member 12 by means of a tapering peg 44 which depends from the lower rear surface 46 of the upper jaw member 16 and is received in a mating socket 48 in the top rear surface 50 of the lower jaw 12. This arrangement allows for the upper jaw 16 to be accurately centered over the lower jaw 12 in order to simulate an ideal bite. The upper jaw 16 may be removed from the lower jaw 12 simply by lifting on the upper jaw until the peg 44 is withdrawn from the socket 48.

In a second embodiment of the invention which is shown in FIGS. 6-9 and indicated in its entirety by the numeral 110, the peg and socket positioning arrangement is replaced by a demountable hinge arrangement 111 for pivotably connecting the upper jaw member 116 to the lower jaw member 112. The hinge arrangement 111 enables a user to simulate the actual biting or talking movements performed by human jaws. Any suitable hinge structure may be used. However, in the illustrated embodiment, the hinge arrangement 111 comprises a cylindrical support member 113 which depends from the bottom rear edge of the upper jaw member 116, a pin member 115 which extends laterally from the support member 113, and a cylindrical sleeve member 117 provided on the upper rear edge of the lower jaw member 112. As is evident from FIG. 7, the pin member 115 is removably receivable in the sleeve member 117 and adapted for rotation therein. However, in yet another embodiment of the invention (not shown), it is possible to make the hinge arrangement 111 non-demountable simply by providing a stop member (not shown) on the end of the pin member 115 to prevent it from being removed from the sleeve member 117. This arrangement may be preferable when the device is intended for use by very small children who might misuse a demountable hinge arrangement by separating the jaw members 112, 116 and losing them.

The device 10 may be provided as part of a kit along with an educational booklet (not shown) including diagrams of the teeth and gums, and illustrating proper brushing and flossing techniques. Dental patients will thus be able to directly relate the diagrams in the book to the actual models of the teeth on the lower and upper jaw members 12 and 16, which will in turn increase their awareness and knowledge of their own teeth and gums and encourage them to develop good dental habits.

In addition, to increase the educational value of the device 10 still further, it may be desirable to provide sufficient spacing between each of the teeth to allow a strand of dental floss to be passed therethrough. This will enable the user to practice flossing techniques on the device before flossing his or her own mouth.

While the principles of the invention have now been made clear in the illustrated embodiments, there will be immediately obvious to those skilled in the art, many modifications of structure, arrangements, proportions, the elements, materials and components used in the practice of the invention and otherwise, which are particularly adapted for specific environments and operation requirements without departing from those principles. The appended claims are therefore intended to cover and embrace any such modifications within the limits only of the true spirit and scope of the invention.

What I claim as my invention:

1. A dental hygiene teaching tool and storage device in the form of a caricatured head comprising:
   (a) a lipless lower jaw member including a front portion and a rear portion, with a set of fully exposed, realistic, simulated human lower gums being formed in said front portion;
   (b) a lipless upper jaw member movably positioned on top of said lower jaw member, said upper jaw member including a front portion and a rear portion, with a realistic palate and a set of fully exposed, realistic, simulated human upper gums being formed in said front portion;
   (c) a set of realistic, orthodontically correct, simulated human teeth, including a set of 16 upper teeth depending from said upper gums of said upper jaw member and a set of 16 lower teeth extending vertically upwardly from said lower gums of said lower jaw member, each set of teeth being symmetrical about an imaginary central axis which divides each jaw into a left side and a right side, with each side of each jaw including three simulated molars, two simulated bicuspids, one simulated cuspid, one simulated lateral tooth, and one simulated central tooth;
   (d) a pair of eyes and a nose formed on the front portion of said upper jaw member above said upper gums to provide said caricatured head with a whimsical facial appearance;
   (e) a well for receiving a container of dental floss; and
   (f) a plurality of elongated bores extending through the rear portion of said upper jaws for receiving a plurality of vertically upstanding, elongated dental hygiene implements.

2. The teaching tool and storage device of claim 1, further comprising positioning means for supporting said upper jaw member in a stable, accurately centered position on top of said lower jaw member.

3. The teaching tool and storage device of claim 2, in which said positioning means comprises:
   (a) a tapered peg depending from the rear portion of said upper jaw member; and
   (b) a socket provided in said lower jaw member for receiving said tapered peg.

4. The teaching tool and storage device of claim 1, further comprising hinge means for pivotably connecting said upper jaw member to said lower jaw member.

5. The teaching tool and storage device of claim 4, in which said hinge means comprises a two-part hinge, with one part of said hinge being connected to the rear portion of said upper jaw member and the other part of said hinge being connected to the rear portion of said lower jaw member, said two parts being demountably attached to one another to allow said upper jaw member to be completely removed from said lower jaw member.

6. The teaching tool and storage device of claim 1, in which said simulated upper and lower teeth are sufficiently spaced from one another to allow a strand of dental floss to pass therebetween.

* * * * *